(12) United States Patent
Reisinger et al.

(10) Patent No.: US 9,088,093 B2
(45) Date of Patent: *Jul. 21, 2015

(54) HEAD PART FOR AN IMPLANTABLE MEDICAL DEVICE

(71) Applicant: Heraeus Precious Metals GmbH & Co. KG, Hanua (DE)

(72) Inventors: Andreas Reisinger, Alzenau (DE); Jeremy Glynn, Buffalo, MN (US)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/293,596

(22) Filed: Jun. 2, 2014

(65) Prior Publication Data

US 2014/0262494 A1    Sep. 18, 2014

Related U.S. Application Data

(63) Continuation of application No. 13/361,355, filed on Jan. 30, 2012, now Pat. No. 8,742,268.

(60) Provisional application No. 61/438,025, filed on Jan. 31, 2011.

(30) Foreign Application Priority Data

Jan. 31, 2011  (DE) .................. 10 2011 009 865

(51) Int. Cl.
*H01R 13/52*  (2006.01)
*A61N 1/375*  (2006.01)
(Continued)

(52) U.S. Cl.
CPC .......... *H01R 13/5224* (2013.01); *A61N 1/3752* (2013.01); *H01R 24/58* (2013.01);
(Continued)

(58) Field of Classification Search
CPC .... H01R 13/5224; H01R 43/20; H01R 24/58; H01R 2201/12

USPC ....................... 174/650; 361/679.1
See application file for complete search history.

(56) References Cited

U.S. PATENT DOCUMENTS 3,979,187 A   9/1976  Scherer
4,152,540 A   5/1979  Duncan et al.
(Continued)

FOREIGN PATENT DOCUMENTS

DE      69729719      7/2005
DE     102006054249   5/2008
(Continued)

OTHER PUBLICATIONS

Restriction Requirement for U.S. Appl. No. 13/361,322 mailed Nov. 14, 2013 (7 pages).
(Continued)

*Primary Examiner* — Dhirubhai R Patel
(74) *Attorney, Agent, or Firm* — Dicke, Billig & Czaja, PLLC

(57) ABSTRACT

An electrical bushing for use in a housing of an implantable medical device is proposed. The electrical bushing includes at least one electrically insulating base body and at least one electrical conducting element. The conducting element establishes, through the base body, at least one electrically conductive connection between an internal space of the housing and an external space. The conducting element is hermetically sealed with respect to the base body, at least in part. The at least one conducting element includes at least one cermet. The electrical bushing includes at least one head part. The head part includes at least one plug connector element that enables electrical connection of at least one plug element from the external space to the plug connector element.

18 Claims, 5 Drawing Sheets

(51) Int. Cl.
  *H01R 24/58* (2011.01)
  *H01R 43/20* (2006.01)
  *A61M 1/12* (2006.01)

(52) U.S. Cl.
  CPC ............... *H01R 43/20* (2013.01); *A61M 1/127* (2013.01); *A61N 1/3754* (2013.01); *H01R 2201/12* (2013.01); *Y10T 29/49169* (2015.01)

(56) References Cited

U.S. PATENT DOCUMENTS

| | | | |
|---|---|---|---|
| 4,217,137 | A | 8/1980 | Kraska et al. |
| 4,315,054 | A | 2/1982 | Sack et al. |
| 4,354,964 | A | 10/1982 | Hing et al. |
| 4,488,673 | A | 12/1984 | Hopper, Jr. |
| 4,602,956 | A | 7/1986 | Partlow et al. |
| 4,678,868 | A | 7/1987 | Kraska et al. |
| 4,991,582 | A | 2/1991 | Byers et al. |
| 5,043,535 | A | 8/1991 | Lin |
| 5,515,604 | A | 5/1996 | Horine et al. |
| 5,738,270 | A | 4/1998 | Malmgren |
| 5,769,874 | A | 6/1998 | Dahlberg |
| 5,796,019 | A | 8/1998 | Lupton et al. |
| 5,861,714 | A | 1/1999 | Wei et al. |
| 5,870,272 | A | 2/1999 | Seifried et al. |
| 6,093,476 | A | 7/2000 | Horiuchi et al. |
| 6,414,835 | B1 | 7/2002 | Wolf et al. |
| 6,643,903 | B2 | 11/2003 | Stevenson et al. |
| 6,660,116 | B2 | 12/2003 | Wolf et al. |
| 6,999,818 | B2 | 2/2006 | Stevenson et al. |
| 7,035,076 | B1 | 4/2006 | Stevenson |
| 7,038,900 | B2 | 5/2006 | Stevenson et al. |
| 7,136,273 | B2 | 11/2006 | Stevenson et al. |
| 7,145,076 | B2 | 12/2006 | Knappen et al. |
| 7,174,219 | B2 | 2/2007 | Wahlstrand et al. |
| 7,174,223 | B2 | 2/2007 | Dalton et al. |
| 7,260,434 | B1 | 8/2007 | Lim et al. |
| 7,274,963 | B2 | 9/2007 | Spadgenske |
| 7,437,817 | B2 | 10/2008 | Zhang et al. |
| 7,480,988 | B2 | 1/2009 | Ok et al. |
| 7,502,217 | B2 | 3/2009 | Zhao et al. |
| 7,561,917 | B2 | 7/2009 | Wegrzyn, III et al. |
| 7,564,674 | B2 | 7/2009 | Frysz et al. |
| 7,630,768 | B1 | 12/2009 | Coffed et al. |
| 7,706,124 | B2 | 4/2010 | Zhao et al. |
| 7,720,538 | B2 | 5/2010 | Janzig et al. |
| 7,736,191 | B1 | 6/2010 | Sochor |
| 7,742,817 | B2 | 6/2010 | Malinowski et al. |
| 7,747,321 | B2 | 6/2010 | Fischbach et al. |
| 7,761,165 | B1 | 7/2010 | He et al. |
| 7,765,005 | B2 | 7/2010 | Stevenson |
| 7,794,256 | B1 * | 9/2010 | Sochor ............ 439/289 |
| 7,901,761 | B1 | 3/2011 | Jiang et al. |
| 7,930,032 | B2 | 4/2011 | Teske et al. |
| 7,970,474 | B2 | 6/2011 | Starke |
| 7,989,080 | B2 | 8/2011 | Greenberg et al. |
| 8,000,804 | B1 | 8/2011 | Wessendorf et al. |
| 8,065,009 | B2 | 11/2011 | Biggs |
| 8,131,369 | B2 | 3/2012 | Taylor et al. |
| 8,131,376 | B1 | 3/2012 | Faraji et al. |
| 8,163,397 | B2 | 4/2012 | Ok et al. |
| 8,179,658 | B2 | 5/2012 | Brendel et al. |
| 8,288,654 | B2 * | 10/2012 | Taylor et al. ......... 174/152 GM |
| 8,346,362 | B2 | 1/2013 | Kinney et al. |
| 8,355,785 | B1 | 1/2013 | Hammond et al. |
| 8,391,983 | B2 | 3/2013 | Lim |
| 8,494,635 | B2 | 7/2013 | Troetzschel et al. |
| 8,497,435 | B2 * | 7/2013 | Nagata et al. ................ 174/650 |
| 8,528,201 | B2 | 9/2013 | Troetzschel et al. |
| 8,552,311 | B2 | 10/2013 | Koester et al. |
| 8,656,736 | B2 | 2/2014 | Terao |
| 8,659,870 | B2 | 2/2014 | Brendel et al. |
| 8,742,268 | B2 | 6/2014 | Reisinger et al. |
| 8,825,162 | B2 | 9/2014 | Reisinger |
| 8,894,914 | B2 | 11/2014 | Pavlovic |
| 2001/0013756 | A1 | 8/2001 | Mori et al. |
| 2004/0116976 | A1 | 6/2004 | Spadgenske |
| 2004/0128016 | A1 | 7/2004 | Stewart |
| 2006/0247714 | A1 | 11/2006 | Taylor et al. |
| 2006/0259093 | A1 | 11/2006 | Stevenson et al. |
| 2007/0183118 | A1 | 8/2007 | Fu et al. |
| 2008/0119906 | A1 | 5/2008 | Starke |
| 2008/0203917 | A1 | 8/2008 | Maya |
| 2008/0269831 | A1 | 10/2008 | Erickson |
| 2009/0192578 | A1 | 7/2009 | Biggs |
| 2009/0281586 | A1 | 11/2009 | Lim |
| 2010/0023086 | A1 | 1/2010 | Lim |
| 2010/0109966 | A1 | 5/2010 | Mateychuk et al. |
| 2010/0258342 | A1 | 10/2010 | Parker |
| 2011/0034965 | A1 | 2/2011 | Troetzschel et al. |
| 2011/0034966 | A1 | 2/2011 | Troetzschel et al. |
| 2011/0048770 | A1 | 3/2011 | Reiterer et al. |
| 2011/0186349 | A1 | 8/2011 | Troetzschel et al. |
| 2012/0127627 | A1 | 5/2012 | Brendel et al. |
| 2012/0193117 | A1 | 8/2012 | Specht et al. |
| 2012/0193118 | A1 | 8/2012 | Kempf et al. |
| 2012/0193119 | A1 | 8/2012 | Kempf et al. |
| 2012/0193125 | A1 | 8/2012 | Pavlovic et al. |
| 2012/0193141 | A1 | 8/2012 | Reisinger et al. |
| 2012/0194981 | A1 | 8/2012 | Kempf et al. |
| 2012/0197326 | A1 | 8/2012 | Pavlovic |
| 2012/0197327 | A1 | 8/2012 | Specht |
| 2012/0197335 | A1 | 8/2012 | Reisinger |
| 2012/0197368 | A1 | 8/2012 | Reisinger |
| 2012/0200011 | A1 | 8/2012 | Pavlovic |
| 2012/0203294 | A1 | 8/2012 | Troetzschel |
| 2014/0368298 | A1 | 12/2014 | Reisinger |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |
| EP | 1754511 | 2/2007 |
| WO | 03073450 | 9/2003 |
| WO | 2004110555 | 12/2004 |
| WO | 2008103166 | 8/2008 |
| WO | 2010091435 | 8/2010 |

OTHER PUBLICATIONS

Office Action for U.S. Appl. No. 13/361,322 mailed Feb. 19, 2014 (26 pages).
Office Action for U.S. Appl. No. 13/361,340 mailed Oct. 25, 2013 (20 pages).
Office Action for U.S. Appl. No. 13/361,340 mailed Apr. 29, 2014 (18 pages).
Restriction Requirement for U.S. Appl. No. 13/361,348 mailed Nov. 14, 2013 (7 pages).
Office Action for U.S. Appl. No. 13/361,348 mailed Feb. 19, 2014 (23 pages).
Office Action for U.S. Appl. No. 13/361,355 mailed date Aug. 7, 2013 (21 pages).
Notice of Allowance for U.S. Appl. No. 13/361,355 mailed Jan. 16, 2014 (18 pages).
Restriction Requirement for U.S. Appl. No. 13/361,362 mailed Nov. 14, 2013 (7 pages).
Office Action for U.S. Appl. No. 13/361,362 mailed Feb. 19, 2014 (19 pages).
Office Action for U.S. Appl. No. 13/361,370 mailed Oct. 29, 2013 (26 pages).
Office Action for U.S. Appl. No. 13/361,370 mailed May 14, 2014 (18 pages).
Restriction Requirement for U.S. Appl. No. 13/361,374 mailed Mar. 5, 2013 (6 pages).

(56) References Cited

OTHER PUBLICATIONS

Office Action for U.S. Appl. No. 13/361,374 mailed Oct. 4, 2013 (22 pages).
Office Action for U.S. Appl. No. 13/361,374 mailed May 1, 2014 (20 pages).
Restriction Requirement for U.S. Appl. No. 13/361,383 mailed Feb. 27, 2013 (6 pages).
Office Action for U.S. Appl. No. 13/361,383 mailed Nov. 13, 2013 (22 pages).
Notice of Allowance for U.S. Appl. No. 13/361,383 mailed Apr. 25, 2014 (18 pages).
Office Action for U.S. Appl. No. 13/361,388 mailed Feb. 11, 2014 (24 pages).
Office Action for U.S. Appl. No. 13/361,398 mailed Mar. 7, 2014 (26 pages).
Restriction Requirement for U.S. Appl. No. 13/361,404 mailed Apr. 8, 2013 (6 pages).
Restriction Requirement for U.S. Appl. No. 13/361,404 mailed Oct. 9, 2013 (5 pages).
Office Action for U.S. Appl. No. 13/361,404 mailed Feb. 27, 2014 (19 pages).
Restriction Requirement for U.S. Appl. No. 13/361,411 mailed Mar. 10, 2014 (7 pages).
Final Office Action for U.S. Appl. No. 13/361,322 mailed Sep. 9, 2014 (17 pages).
Final Office Action for U.S. Appl. No. 13/361,340 mailed Oct. 30, 2014 (21 pages).
Final Office Action for U.S. Appl. No. 13/361,348 mailed Sep. 9, 2014 (19 pages).
Final Office Action for U.S. Appl. No. 13/361,362 mailed Sep. 9, 2014 (19 pages).
Final Office Action for U.S. Appl. No. 13/361,370 mailed Nov. 5, 2014 (19 pages).
Final Office Action for U.S. Appl. No. 13/361,374 mailed Nov. 10, 2014 (19 pages).
Final Office Action for U.S. Appl. No. 13/361,388 mailed Jul. 31, 2014 (32 pages).
Notice of Allowance for U.S. Appl. No. 13/361,398 mailed Jul. 25, 2014 (11 pages).
Final Office Action for U.S. Appl. No. 13/361,404 mailed Oct. 9, 2014 (12 pages).
Office Action for U.S. Appl. No. 13/361,411 mailed Aug. 1, 2014 (18 pages).
Office Action for U.S. Appl. No. 13/361,322 mailed Feb. 4, 2015 (19 pages).
Notice of Allowance for U.S. Appl. No. 13/361,348 mailed Jan. 22, 2015 (9 pages).
Notice of Allowance for U.S. Appl. No. 13/361,404 mailed Jan. 28, 2015 (6 pages).
Notice of Allowance for U.S. Appl. No. 13/361,411 mailed Jan. 20, 2015 (8 pages).
Office Action for U.S. Appl. No. 13/361,388 mailed Feb. 9, 2015 (19 pages).
Hussain, et al., "Electrical conductivity of an insulator matrix (alumina) and conductor particle (molybdenum) composites", Journal of the European Ceramic Society, vol. 23, Issue 2, Feb. 2003, pp. 315-321.

* cited by examiner

HEAD PART FOR AN IMPLANTABLE MEDICAL DEVICE

CROSS-REFERENCE TO RELATED APPLICATIONS

This application is a continuation of U.S. patent application Ser. No. 13/361,355, now U.S. Pat. No. 8,742,268, entitled "HEAD PART FOR AN IMPLANTABLE MEDICAL DEVICE," having a filing date of Jan. 30, 2012, which claims the benefit of the filing date of U.S. Provisional Patent Application Ser. No. 61/438,025, filed Jan. 31, 2011, entitled "HEAD PART FOR AN IMPLANTABLE MEDICAL DEVICE," which claims priority to German Patent Application No. DE 10 2011 009 865.8, filed on Jan. 31, 2011, and all of which are incorporated herein by reference.

This patent application is also related to patent application Ser. No. 13/361,322 filed on Jan. 30, 2012, entitled "CERAMIC BUSHING FOR AN IMPLANTABLE MEDICAL DEVICE"; patent application Ser. No. 13/361,340 filed on Jan. 30, 2012, entitled "DIRECTLY APPLICABLE ELECTRICAL BUSHING"; patent application Ser. No. 13/361,348 filed on Jan. 30, 2012, entitled "IMPLANTABLE DEVICE HAVING AN INTEGRATED CERAMIC BUSHING"; patent application Ser. No. 13/361,362 filed on Jan. 30, 2012, entitled "CERMET-CONTAINING BUSHING FOR AN IMPLANTABLE MEDICAL DEVICE HAVING A CONNECTING LAYER"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE"; patent application Ser. No. 13/361,374 filed on Jan. 30, 2012, entitled "CERAMIC BUSHING WITH FILTER"; patent application Ser. No. 13/361,383 filed on Jan. 30, 2012, entitled "CERAMIC BUSHING WITH INDUCTIVE FILTER"; patent application Ser. No. 13/361,388 filed on Jan. 30, 2012, entitled "CERAMIC BUSHING HAVING HIGH CONDUCTIVITY CONDUCTING ELEMENTS"; patent application Ser. No. 13/361,398 filed on Jan. 30, 2012, entitled "METHOD FOR THE MANUFACTURE OF A CERMET-CONTAINING BUSHING"; patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE"; and patent application Ser. No. 13/361,411 filed on Jan. 30, 2012, entitled "CERMET-CONTAINING BUSHING WITH HOLDING ELEMENT FOR AN IMPLANTABLE MEDICAL DEVICE".

BACKGROUND

One aspect relates to an implantable medical device and an electrical bushing for use in a housing of an implantable medical device. Moreover, one aspect relates to a method for the manufacture of an electrical bushing for an implantable medical device.

The post-published document, DE 10 2009 035 972, discloses an electrical bushing for an implantable medical device having the features of the preamble of claim 1. Moreover, a use of at least one cermet-comprising conducting element in an electrical bushing for an implantable medical device and a method for the manufacture of an electrical bushing for an implantable medical device are disclosed.

A multitude of electrical bushings for various applications are known, examples including: U.S. Pat. Nos. 4,678,868, 7,564,674 B2, US 2008/0119906 A1, U.S. Pat. Nos. 7,145,076 B2, 7,561,917, US 2007/0183118 A1, U.S. Pat. Nos. 7,260,434B1, 7,761,165, 7,742,817 B2, 7,736,191 B1, US 2006/0259093 A1, U.S. Pat. No. 7,274,963 B2, US 2004116976 A1, U.S. Pat. No. 7,794,256, US 2010/0023086 A1, U.S. Pat. Nos. 7,502,217 B2, 7,706,124 B2, 6,999,818 B2, EP 1754511 A2, U.S. Pat. No. 7,035,076, EP 1685874 A1, WO 03/073450 A1, U.S. Pat. Nos. 7,136,273, 7,765,005, WO 2008/103166 A1, US 2008/0269831, U.S. Pat. No. 7,174,219 B2, WO 2004/110555 A1, U.S. Pat. No. 7,720,538 B2, WO 2010/091435, US 2010/0258342 A1, US 2001/0013756 A1, U.S. Pat. No. 4,315,054, and EP 0877400.

From DE 10 2008 021 064 A1 is known a connection housing for an electrical medical implant having contact sockets for accommodating and contacting electrode lead plugs. The connection housing includes a base module and a separately fabricated lid module, which is inserted into the base module and connected to it and has a contact socket that complies with the IS-4 standard.

From US 2008/0119906 A1 is known a hermetically sealed electrical bushing for cardiac pacemakers and defibrillators. Said bushing includes a flat ceramic disc that is used as an insulating support. The insulating disc includes openings, into which various electrodes are inserted as through-going contacts. Moreover, a metal flange is disclosed through which the ceramic disc can be connected to a housing.

From U.S. Pat. No. 7,260,434 is known a bushing device for an implantable medical device. It includes a plurality of filtered feedthrough arrangements each of which extends through an insulating base.

DE 697 297 19 T2 describes an electrical bushing for an active implantable medical device—also called implantable device or therapeutic device.

Electrical bushings generally serve to establish an electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one of its sides. Said connection body includes a hollow space having at least one connection socket or plug socket for connecting electrode leads. In this context, the connection socket includes electrical contacts in order to electrically connect the electrode leads to the control electronics on the interior of the housing of the implantable therapeutic device. Usually, hermetic sealing with respect to a surrounding is an essential prerequisite of an electrical bushing of this type. Therefore, lead wires that are introduced into an electrically insulating base body—also called signal-transmission elements—through which the electrical signals are propagated, must be introduced into the base body, usually such as to be free of gaps.

In this context, it has proven to be challenging that the lead wires generally are made of a metal and are introduced into a ceramic base body. In order to ensure durable connection between the two elements, the internal surface of a through-opening—also called openings—in the base body is metallized in order to attach the lead wires by soldering. However, the metallization in the through-opening has proven to be difficult to apply. Only expensive procedures ensure homogeneous metallization of the internal surface of the bore hole—and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

DETAILED DESCRIPTION

Figure 1:
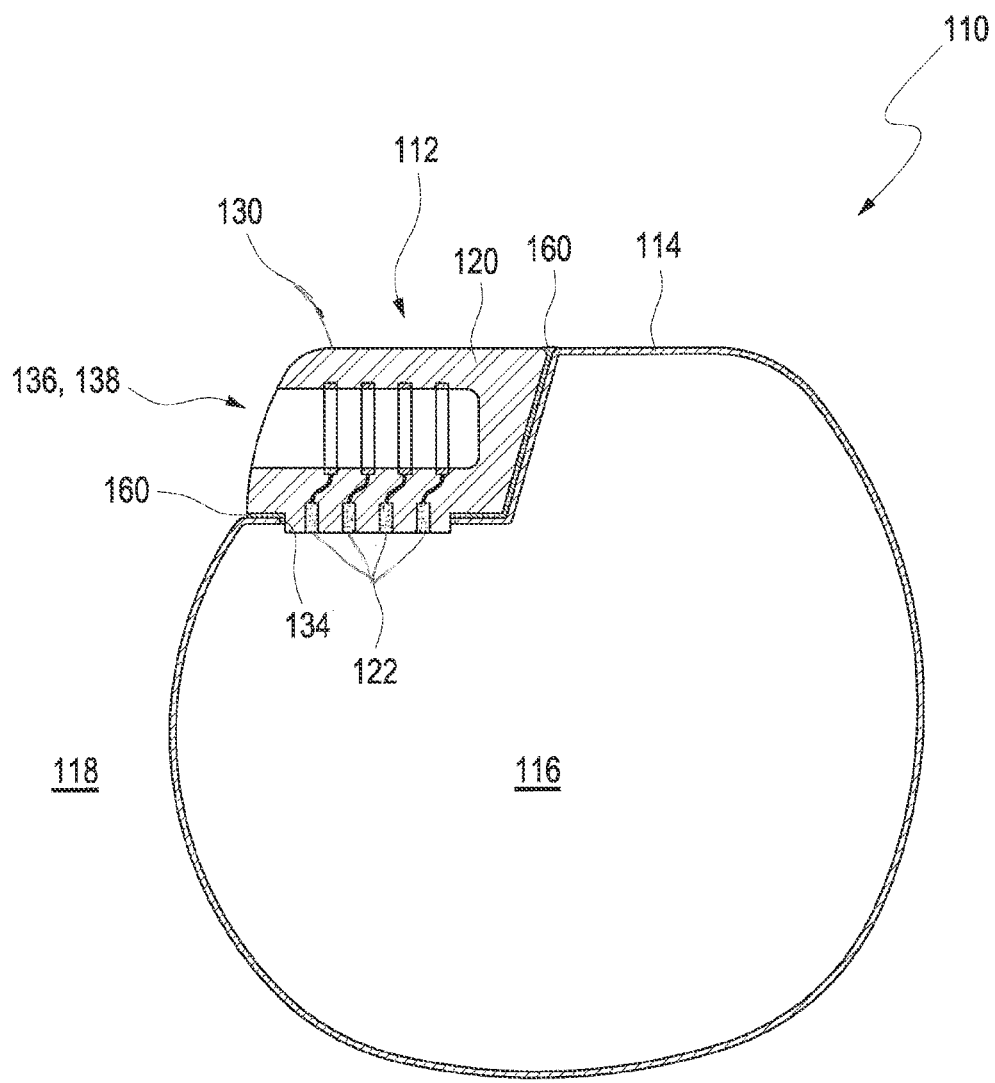
FIGS. 1 and 2 illustrate various views of a first exemplary embodiment of an implantable medical device and of an electrical bushing according to an embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One aspect is to specify an electrical bushing for use in a housing of an implantable medical device, which circumvents the disadvantages of known devices of the above-mentioned type at least in part. For example, an electrical bushing for use in a housing of an implantable medical device is to be proposed that is easy to manufacture, highly sealed, and, furthermore, enables external components to be connected easily.

An electrical bushing for use in a housing of an implantable medical device, an implantable medical device, and a method for the manufacture of an electrical bushing having the features of the independent claims are proposed. Refinements of the embodiments, which can be implemented alone or in combination, are specified in the dependent claims. Features and details that are described in the context of the electrical bushing or the implantable medical device shall also apply in relation to the method, and vice versa.

In summary, the following embodiments are proposed:

Embodiment 1: An electrical bushing for use in a housing of an implantable medical device;

whereby the electrical bushing includes at least one electrically insulating base body and at least one electrical conducting element;

whereby the conducting element establishes, through the base body, at least one electrically conductive connection between an internal space of the housing and an external space;

whereby the conducting element is hermetically sealed, at least in part, with respect to the base body;

whereby the at least one conducting element includes at least one cermet;

characterized in that the electrical bushing includes at least one head part, whereby the head part includes at least one plug connector element, whereby the plug connector element is set up to enable electrical connection of at least one plug element from the external space to the plug connector element.

Embodiment 2: Electrical bushing according to the preceding embodiment, characterized in that the conducting element includes at least one feedthrough element, whereby the feedthrough element includes the at least one cermet.

Embodiment 3: Electrical bushing according to the preceding embodiment, characterized in that the feedthrough element is embedded in the base body.

Embodiment 4: Electrical bushing according to any one of the two preceding embodiments, characterized in that the feedthrough element and the base body are connected in a firmly bonded manner, for example, through a firmly bonded sintered connection.

Embodiment 5: Electrical bushing according to any one of the three preceding embodiments, characterized in that the feedthrough element can be electrically contacted from the internal space.

Embodiment 6: Electrical bushing according to any one of the preceding four embodiments, characterized in that the feedthrough element and the plug connector element are connected in an electrically conductive manner, for example, through at least one connecting element and through at least one connecting wire.

Embodiment 7: Electrical bushing according to any one of the preceding embodiments, characterized in that the connecting element includes at least one metallic material, for example, at least one metallic connecting wire, whereby the metallic material is selected from the group consisting of: platinum; a platinum alloy; iridium; niobium; molybdenum; titanium; a titanium alloy; tantalum; a tantalum alloy; tungsten; a tungsten alloy; stainless steel; a cobalt-chromium alloy.

Embodiment 8: Electrical bushing according to any one of the six preceding embodiments, characterized in that the feedthrough element is flush with a surface of the base body or projects beyond the surface, for example, into the internal space and/or the external space of the housing.

Embodiment 9: Electrical bushing according to any one of the preceding embodiments, characterized in that the cermet includes at least one metallic component, whereby the metallic component is selected from the group consisting of: platinum, a platinum alloy, iridium, niobium, molybdenum, titanium, a titanium alloy, cobalt, zirconium, chromium, tantalum, a tantalum alloy, tungsten, a tungsten alloy.

Embodiment 10: Electrical bushing according to any one of the preceding embodiments, characterized in that the cermet includes at least one ceramic component selected from the group consisting of: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of Ba $(Zr, Ti)O_3$, Ba $(Ce, Ti)O_3$, KNN, KNN—$LiSbO_3$, and KNN—$LiTaO_3$.

Embodiment 11: Electrical bushing according to any one of the preceding embodiments, characterized in that the plug connector element includes at least 2 contact elements, in one embodiment, at least 4 contact elements, in one embodiment, at least 8 contact elements, in one embodiment, at least 16 contact elements, in one embodiment, at least 32 contact elements, in one embodiment, at least 64 contact elements, and in one embodiment, at least 128 contact elements.

Embodiment 12: Electrical bushing according to any one of the preceding embodiments, characterized in that the plug connector element includes at least one plug socket.

Embodiment 13: Electrical bushing according to the preceding embodiment, characterized in that the plug socket includes at least one contact element of the conducting element that can be contacted by the plug connector element.

Embodiment 14: Electrical bushing according to the preceding embodiment, characterized in that the contact element is provided to be ring-shaped.

Embodiment 15: Electrical bushing according to any one of the two preceding embodiments, characterized in that the plug socket includes a hollow space that is accessible from the external space, whereby the contact element is arranged in said hollow space, at least in part.

Embodiment 16: Electrical bushing according to any one of the preceding embodiments, characterized in that the head part is made as a single part from a plastic material, at least in part.

Embodiment 17: Electrical bushing according to any one of the preceding embodiments, characterized in that the head part is made from an insulating composition of materials, at least in part, whereby it is preferred in one embodiment for the base body to also be made from the insulating composition of materials, at least in part.

Embodiment 18: Electrical bushing according to the preceding embodiment, characterized in that the insulating composition of materials is selected from the group consisting of: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of Ba $(Zr, Ti)O_3$, Ba $(Ce, Ti)O_3$, KNN, KNN—$LiSbO_3$, and KNN—$LiTaO_3$.

Embodiment 19: Electrical bushing according to any one of the preceding embodiments, characterized in that the head part includes at least one first component, whereby the first component and the base body are provided as a single part, whereby the head part further includes at least one second component, whereby the second component is connected to the first component and, jointly with the first component provides the plug connector element or a part thereof.

Embodiment 20: Electrical bushing according to the preceding embodiment, characterized in that at least one contact element of the conducting element is arranged between the first component and the second component.

Embodiment 21: Electrical bushing according to any one of the two preceding embodiments, characterized in that the at least one contact element of the conducting element is introduced into the first component through at least one mounting opening of the first component, whereby the second component includes at least one closure, for example, at least one filling material, whereby the closure closes the mounting opening, at least in part.

Embodiment 22: Electrical bushing according to any one of the three preceding embodiments, characterized in that the second component is made from a plastic material, at least in part.

Embodiment 23: Electrical bushing according to the preceding embodiment, characterized in that the plastic material is selected from the group consisting of: a polyurethane, for example, Tecothane®; a silicone; an epoxy resin.

Embodiment 24: Electrical bushing according to any one of the two preceding embodiments, characterized in that the plastic material is an optically transparent plastic material.

Embodiment 25: Electrical bushing according to any one of the five preceding embodiments, characterized in that the first component includes a lower shell, whereby the second component includes an upper shell, whereby at least one hollow space of the plug connector element, for example, at least one hollow space of at least one plug socket of the plug connector element, is arranged between the lower shell and the upper shell.

Embodiment 26: Electrical bushing according to any one of the preceding embodiments, characterized in that the electrical bushing further includes at least one filter element, for example, a filter element selected from the group consisting of: a high-pass filter, a low-pass filter, a band-pass filter.

Embodiment 27: Implantable medical device, comprising at least one housing and at least one electrical bushing according to any one of the preceding embodiments, whereby the electrical bushing is connected to the housing.

Embodiment 28: Implantable medical device according to the preceding embodiment, further comprising at least one frame, whereby the frame surrounds the electrical bushing at least in part, whereby the electrical bushing is connected to the housing by means of the frame.

Embodiment 29: Implantable medical device according to the preceding embodiment, characterized in that the frame includes at least one metallic material, for example, a metallic material selected from the group consisting of: niobium; a niobium alloy; molybdenum; a molybdenum alloy; titanium; a titanium alloy; tantalum; a tantalum alloy; stainless steel; a cobalt-chromium alloy.

Embodiment 30: Implantable medical device according to any one of the preceding embodiments that are related to an implantable medical device, characterized in that the electrical bushing is connected to an inside facing the internal space and/or an outside of the housing facing the external space through at least one firmly bonded connection, for example, through at least one solder connection.

Embodiment 31: Implantable medical device according to the preceding embodiment, characterized in that the electrical bushing, for example, the base body of the electrical bushing, includes a metallization, for example, a gold metallization, at least at the site of the firmly bonded connection.

Embodiment 32: Implantable medical device according to any one of the two preceding embodiments, characterized in that the firmly bonded connection surrounds at least one opening of the plug connector element that is accessible from the external space, for example, at least one opening of at least one plug socket of the plug connector element.

Embodiment 33: Implantable medical device according to any one of the preceding embodiments that are related to an implantable medical device, characterized in that the implantable medical device is selected from the group consisting of: an active implantable device for transmitting an electrical stimulation to a body tissue, for example, a muscle, a nerve, a brain region or a blood vessel; a cardiac pacemaker; an implantable defibrillator; a device against congestive heart failure; a hearing aid; a cochlea implant; a retina implant; a neuro-stimulator; a peripheral muscle stimulator; a drug pump, for example, an insulin pump; a ventricular aiding device; a spinal marrow stimulator; an implantable sensor system; an artificial heart; an incontinence device; a bone growth stimulator; a gastric pacemaker; a prosthetic device.

Embodiment 34: Implantable medical device according to any one of the preceding embodiments that are related to an implantable medical device, characterized in that the head part projects into the internal space and/or the external space.

Embodiment 35: Method for the manufacture of an electrical bushing according to any one of the preceding embodiments that are related to an electrical bushing, characterized in that the method includes the following steps:
  a. manufacturing the at least one first component of the head part and of the base body through at least one ceramic manufacturing procedure, whereby the first component and the base body are provided as a single part; and
  b. connecting at least one contact element of the conducting element to the first component.

Embodiment 36: Method according to the preceding embodiment, characterized in that the contact element is to be connected to at least one feedthrough element that contains the cermet and is embedded in the base body.

Embodiment 37: Method according to any one of the two preceding embodiments, characterized through the following further step:
  c. connecting at least one second component of the head part to the first component.

Embodiment 38: Method according to the preceding embodiment, characterized in that the second component is provided, at least in part, as a pre-formed component which is connected to the first component in step c.

Embodiment 39: Method according to any one of the two preceding embodiments, characterized in that the second component is formed, at least in part, in procedural step c., for example, through a plastic forming procedure.

Embodiment 40: Method according to any one of the three preceding embodiments, characterized in that the second component is connected to the first component in a firmly bonded manner in procedural step c., for example, through a firmly bonding procedure selected from the group consisting of: a casting procedure; an injection molding procedure; a gluing procedure.

Embodiment 41: Method according to any one of the four preceding embodiments, characterized in that the contact element is introduced into at least one opening in the first component in procedural step b., whereby the opening is closed, at least in part, through at least one closure in the subsequent procedural step c., for example, through at least one grouting, whereby the second component includes the closure.

The proposed electrical bushing is set up for use in an implantable medical device, that is, for application in an implantable medical device, whereby the implantable medical device can be provided, for example, as an active implantable medical device (AIMD) and in one embodiment as a therapeutic device.

As a matter of principle, the term, implantable medical device, shall include any device which is set up to perform at least one medical function and which can be introduced into a body tissue of a human or animal user. As a general rule, the medical function can include any function selected from the group consisting of a therapeutic function, a diagnostic function, and a surgical function. For example, the medical function can include at least one actuator function, in which an actuator is used to exert at least one stimulus on the body tissue, for example, an electrical stimulus.

As a matter of principle, the term, active implantable medical device—also called AIMD—shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, can usually include, for example, at least one housing, for example, at least one hermetically sealed housing. The housing can in one embodiment enclose at least one electronics unit, for example a triggering and/or analytical electronics unit of the implantable medical device.

According to the scope of one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element from stresses occurring during operation and/or handling, and/or protection to the functional element from influences of its surroundings such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can include at least one hollow space which can be closed fully or in part. However, alternatively, the internal space can be filled up fully or in part, for example by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing and/or, for example, the electrical bushing can, for example, be provided to be hermetically sealed such that, for example, the internal space, is hermetically sealed with respect to the external space. In this context, the term, "hermetically sealed", can illustrate that moisture and/or gases cannot permeate through the hermetically sealed element at all or only to a minimal extent upon the intended use for the common periods of time (for example 5-10 years). The so-called leak rate, which can be determined, for example, by leak tests, is a physical parameter that can describe, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of one embodiment, said maximal permissible helium leak rates can, for example, be from $1\times10^{-8}$ atm*cm$^3$/sec to $1\times10^{-7}$ atm*cm$^3$/sec. In the scope of one embodiment, the term, "hermetically sealed", shall be understood, for example, to mean that the device to be tested (for example the housing and/or the electrical bushing and/or the housing with the electrical bushing) has a helium leak rate of less than $1\times10^{-7}$ atm*cm$^3$/sec. In one embodiment, the helium leak rate can be less than $1\times10^{-8}$ atm*cm$^3$/sec, in one embodiment, less than $1\times10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

As illustrated above, the conducting element is hermetically sealed with respect to the base body, at least in part. In this context, hermetic sealing shall be understood to mean a sealing, which in one embodiment is designed to be hermetically sealed, in one embodiment as such and without any contribution of further elements, whereby reference shall be made to the definition provided above with regard to the term, "hermetically sealed". However, in addition, the term, "hermetically sealed, at least in part" can include refinements, in which the conducting element is hermetically sealed with respect to the electrically insulating base body involving a contribution of one or more further element(s).

Electrical bushings are elements set up to create at least one electrically conducting path that extends between the internal space of the housing to at least one external point or region outside the housing, for example, situated in the external space. Accordingly, this establishes, for example, an electrical connection to leads, electrodes, and sensors that are arranged outside the housing.

Common implantable medical devices are commonly provided with a housing, which can include, on one side, a head part, also called header or connecting body, that carries plug sockets for connection of leads, also called electrode leads. The plug sockets include, for example, electrical contacts that serve to electrically connect the leads to a control electronics unit on the interior of the housing of the medical device. Usually, an electrical bushing is provided in any place, in which the electrical connection enters the housing of the medical device, and the electrical bushing is inserted into a corresponding opening of the housing in a hermetically sealing manner.

Due to the type of use of implantable medical devices, their hermetic sealing and biocompatibility are usually amongst the foremost requirements. The implantable medical device proposed herein according to one embodiment, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device, and thus the electrical bushing as well, should be as impermeable as possible, for example, with respect to body fluids.

Moreover, the electrical bushing should ensure high electrical insulation between the at least one conducting element and the housing and/or the multiple conducting elements provided that more than one conducting element are present. In this context, the insulation resistance reached in one embodiment is at least several MOhm, for example, more than 20 MOhm, and the leakage currents reached can be small, for example, less than 10 pA. Moreover, in case multiple conducting elements are present, the crosstalk and electromagnetic coupling between the individual conducting elements in one embodiment are below the specified thresholds for medical applications.

The electrical bushing disclosed according to one embodiment is well-suited for the above-mentioned applications. Moreover, the electrical bushing can also be used in other applications that are associated with special requirements with regard to biocompatibility, tight sealing, and stability.

The electrical bushing according to one embodiment can meet, for example, the above-mentioned tight sealing requirements and/or the above-mentioned insulation requirements.

As mentioned above, the electrical bushing includes at least one electrically insulating base body. In the scope of one embodiment, a base body shall be understood to mean an element that serves a mechanical holding function in the electrical bushing, for example in that the base body holds or carries the at least one conducting element either directly or indirectly. For example, the at least one conducting element can be embedded in the base body directly or indirectly, fully or partly, for example, through a firmly bonded connection between the base body and the conducting element and in one embodiment through co-sintering of the base body and the conducting element. For example, the base body can have at least one side facing the internal space and at least one side facing the external space and/or accessible from the external space.

As mentioned above, the base body is provided to be electrically insulating. This means that the base body, fully or at least regions thereof, is made from at least one electrically insulating material. In this context, an electrically insulating material shall be understood to mean a material with a resistivity of at least $10^7$ Ohm*m, in one embodiment, of at least $10^8$ Ohm*m, in one embodiment of at least $10^9$ Ohm*m, and in one embodiment of at least $10^{11}$ Ohm*m. For example, the base body can be provided such that, as mentioned above, a flow of current between the conducting element and the housing and/or between multiple conducting elements is prevented, at least largely, for example through the resistivity values between the conducting element and the housing as specified above being implemented. For example, the base body can include at least one ceramic material.

In this context, a conducting element or electrical conducting element shall generally be understood to mean an element set up to establish an electrical connection between at least two sites and/or at least two elements. For example, the conducting element can include one or more electrical conductors, for example metallic conductors. In the scope of one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side of the base body and/or electrical bushing facing the internal space or on a side of the base body and/or electrical bushing facing the external space or accessible from the external space, one or more connecting contacts, for example one or more plug-in connectors, for example one or more connecting contacts, which project from the base body or can be electrically contacted through other means from the internal space and/or the external space.

The at least one conducting element can establish the electrically conductive connection between the internal space and the external space in a variety of ways. For example, the conducting element can extend from at least one section of the conducting element that is arranged on the side of the base body facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other. Various exemplary embodiments shall be illustrated in more detail below.

The at least one conducting element can include, on a side of the base body and/or electrical bushing facing the internal space or on a side of the base body and/or electrical bushing facing the external space or accessible from the external space, at least one electrical connecting element and/or be connected to an electrical connecting element of this type. For example, as described above, one or more plug-in connectors and/or one or more contact surfaces and/or one or more contact springs and/or one or more types of electrical connecting elements can be provided on one or both of said sides. The at least one optional connecting element can, for example, be a component of the at least one conducting element and/or can be connected to the at least one conducting element in an electrically conducting manner. For example, one or more conducting elements of the bushing can be contacted to one or more internal connecting elements and/or one or more external connecting elements. The material of the internal connecting elements should be suited for permanent connection to the conducting element. The external connecting elements should be biocompatible and should be such that they can be permanently connected to the at least one conducting element.

The electrical bushing can include at least one filter element, as illustrated, for example, in embodiment 26. Said at least one filter element can be set up to subject electrical signals, which are conducted through the electrical bushing, to a filtering, for example, a frequency filtering. The at least one filter element can, for example, be arranged on a side of the electrical bushing that faces the internal space and/or on a side that faces the external space. Alternatively or in addition, the at least one filter element can just as well be integrated into the electrical bushing itself, for example in that same is also embedded into the base body. Designing filter elements by means of corresponding electrical elements, for example through at least one capacitor and at least one ohmic resistor and/or through an inductor and at least one ohmic resistor is basically known to the person skilled in the art. With regard to possible refinements of the filter elements, reference shall also be made to the above-mentioned references, for example, to U.S. Pat. No. 7,260,434.

In the scope of one embodiment, a head part shall be understood to mean an element that can act as an integral part of one or more electrical plug connections of an implantable medical device. The head part, for example, can project from the housing and can be arranged fully or in part on the housing or in the external space, but, as a general rule, it can just as well project into the internal space such that the plug connection is accessible, for example, through an opening in the housing. Exemplary embodiments shall be illustrated in more detail below. With regard to possible embodiments with regard to the shape of the head part, reference shall be made, for example, to DE 10 2008 021 064 A1 mentioned above. However, other designs are also feasible as a matter of principle.

The at least one plug connection can be provided, for example, to comply with one or more of the following standards: IS-4 standard, IS-1 and/or ISO 5841-3 standard, DF-1 and/or ISO 11318:1993 standard. In case multiple plug connections are provided, at least one, in one embodiment more and in one embodiment all of said plug connections can be provided to comply with one or more of said standards. IS-1 is an international standard for connectors (ISO 5841-3) that ensures that cardiac pacemakers and electrodes conforming to the standard match mechanically. DF-1 is an international standard for connectors (ISO 11318:1993) that ensures that cardiac pacemakers and electrodes conforming to the standard match mechanically.

A plug connector element shall generally be understood to be an element set up to undergo an electrical plug connection with at least one further plug connector element. The plug connection can be provided to be of a single-pole or, in one embodiment, multi-pole type. The plug connector element of the head part of the electrical bushing can be provided, for example, fully or in part as female plug connector element. The plug connector element can be provided, for example, fully or in part to comply with one or more of the above-mentioned standards.

As described above, the conducting element can be provided, for example, in the form of multiple parts. Accordingly, as described above and illustrated for example, for example, in embodiment 2, the conducting element can include the at least one feedthrough element, which, in turn, includes the at least one cermet, that is, is made from the at least one cermet either fully or in part. Alternatively or in addition, the conducting element can include one or more further element(s), which also can be made from at least one cermet either fully or in part, but which can be made, as a general rule, for example, in any other manner, for example from at least one metallic material without a ceramic component.

For example, the conducting element can include at least one contact element, as is illustrated, for example, in embodiments 11 or 13 above. For example, 2 contact elements, more than 2 contact elements, 4 contact elements, more than 4 contact elements, 8 contact elements, more than 8 contact elements, 16 contact elements, more than 16 contact elements, 32 contact elements, more than 32 contact elements, 64 contact elements, more than 64 contact elements, 128 contact elements or more than 128 contact elements can be provided. This can lead to a number of channels being provided per plug connector element that corresponds to the number of contact elements. The at least one contact element can be made, for example, fully or partly from at least one metallic material without any ceramic component. A contact element shall generally be understood to mean an electrically conductive element that is an integral part of the plug connector element and is thus set up to be electrically contacted directly or indirectly from the external space. The at least one contact element can basically take any shape, whereby the ring shape specified above is used in one embodiment. However, alternatively or in addition, the at least one contact element can just as well take a rod shape, a shape of a contact spring, a shape of a contact surface that is accessible from the external space or any other shape.

As illustrated in exemplary embodiment 6, the conducting element can include, in addition, one or more further elements, for example the at least one connecting element for establishing an electrical connection between the feedthrough element and the plug connector element, for example, the at least one contact element of the plug connector element. Said connecting element can, for example, also be made from a metallic material, for example from a metallic material without a ceramic component. Said connecting element can include, for example, at least one connecting wire. However, alternatively or in addition, the connecting element can include other components as well. Accordingly, an electrical connection can be established between the contact element and the feedthrough element by means of an electrical clamping connection, a screw connection, a plug connection or any other firmly bonded, non-positive fit-type and/or positive fit-type connection having electrically conductive properties, for example a conductive adhesive, a solder connection or any other type of connection.

In the scope of one embodiment, a plug socket shall generally be understood to be a socket that can be used to establish an electrical plug connector. A socket shall generally be understood to mean an external element of a plug connector, into which at least one plug can be plugged or inserted. Accordingly, in the scope of one embodiment, the plug socket can include at least one external element, into which at least one connector or at least a part of a connector can be plugged or inserted. Said external element can fully or partly surround the plug, which can be provided in the form of a single part or multiple parts and can include one or more contacts, and thus establish the at least one plug connection. The term, plug socket, can be used synonymously with other terms of similar or equal meaning such as, for example, the term, connection socket or contact socket.

Said plug socket can, for example, be a standardized plug socket or include at least one standardized plug socket. If multiple plug sockets are provided, in one embodiment one, more or all plug sockets are provided to be standardized. The standardization can, for example, be selected from one or more of the following standards: IS-4 standard, IS-1 and/or ISO 5841-3 standard, DF-1 and/or ISO 11318:1993 standard. However, this can also include other types of plug sockets alternatively or in addition.

The optional hollow space of the plug socket according to embodiment 15 can include, for example, at least one opening towards the external space. The plug socket and/or the opening can basically have any cross-section, for example a cross-section that is circular, oval, polygonal or of any other shape. One or more plug sockets can be provided, for example, having one or more hollow spaces and/or one or more openings. If multiple plug sockets are provided, these can be provided separately or can be combined fully or partly.

As illustrated above, the head part and the base body can be provided, for example, as a single part, at least in part. This can be effected, for example, in that the head part or at least a part of the head part, which, together with the base body, is provided as a single part, is formed together with the base body in a procedure, for example a ceramic manufacturing procedure. For example, at least one first component and the base body can be provided as a single part. Moreover, one or more second component(s) can be provided, which are not provided as the same part as the base body. In this context, the terminology of "first" and "second" component shall be understood to be for purpose of naming only without any reference being made to numbering and without a second component necessarily having to be provided, in case a first component is present. An arrangement "between" the first component and the second component in embodiment 20 shall be understood to mean an arrangement, in which the contact element extends between the first component and the second component, for example in that said contact element touches both components. In one embodiment, the first component and the second component are electrically insulating in the sense of the definition provided above.

The optional second component can be provided as a prefabricated or pre-formed component to be connected to the first component. This can be effected, for example, like in embodiment 25 described above or in other refinements. Alternatively or in addition, the second component can just as well be formed, either fully or in part, only upon being connected to the first component. This can be effected in a variety of ways. The second component can, for example and as illustrated in embodiment 21, be designed as a closure either fully or in part, for example as filling material and for example, as grouting compound, for example as closure of at least one mounting opening of the first component, after introduction of the at least one contact element.

The electrically insulating base body can support, as a bearing, and/or surround, at least in part, for example, the at least one conducting element. The at least one material of the base body in one embodiment is biocompatible, as illustrated above, and should have sufficiently high insulation resistance. It has proven to be advantageous in one embodiment for the base body to include one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3$/$ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate.

With regard to possible refinements of the cermet and/or metal materials and/or components that are used, reference shall be made to the embodiments specified above. Combinations of multiple possibilities specified above are conceivable as well. In this context, ZTA shall be understood to mean zirconium-toughened alumina (Zirkonia Toughened Alumina), that is, a material, in which zirconium oxide is embedded in an aluminum oxide matrix, for example 10-30% by volume zirconium dioxide in an aluminum oxide matrix. In this context, ATZ shall be understood to mean alumina-toughened zirconia, that is, a material, in which aluminum oxide is embedded in a zirconium oxide matrix, for example at a fraction of 10-30% by volume. Y-TZP shall be understood to mean yttrium-toughened zirconium oxide, that is, zirconium oxide comprising an yttrium fraction. KNN means potassium-sodium niobate.

The base body can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors with no ceramic fraction.

In the scope of one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added. The ceramic powder or powders of the cermet in one embodiment have a mean grain size of less than 10 μm, in one embodiment less than 5 μm, and in one embodiment less than 3 μm. The metallic powder or powders of the cermet in one embodiment have a mean grain size of less than 15 μm, in one embodiment less than 10 μm, and in one embodiment less than 5 μm. For production of a base body, for example, at least one ceramic powder can be used to which, for example, at least one binding agent and, if applicable, at least one solvent can be added. In this context, the ceramic powder or powders in one embodiment has/have a mean grain size of less than 10 μm (1 μm is equal to $1 \times 10^{-6}$ m), in one embodiment less than 5 μm, in one embodiment less than 3 μm. For example, the median value or the d50 value of the grain size distribution is considered to be the mean grain size in this context. The d50 value corresponds to the value at which 50 percent of the grains of the ceramic powder and/or metallic powder are finer and 50% are coarser than the d50 value.

In the scope of one embodiment, a ceramic manufacturing method shall be understood to mean a procedure that includes at least one sintering process of at least one insulating and/or at least one electrically conductive material, for example, at least one ceramic material. As shall be explained in more detail below, said ceramic manufacturing method can, for example, include a forming for the manufacture of at least one form body, for example one ceramic green compact and/or at least one ceramic brown compact.

In the scope of one embodiment, a sintering or a sintering process shall generally be understood to mean a procedure for the manufacture of materials or work-pieces, in which powdered, for example, fine-grained, ceramic and/or metallic substances are heated and connected in the process. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, for example, at least 100 bar, or even at least 1000 bar. The process can proceed, for example, fully or partly, at temperatures below the melting temperature of the powdered materials, for example at temperatures of 700° C. to 1400° C. The process can be carried out, for example, fully or partly, in a tool and/or a mold such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

A method can be used, for example, in the manufacture of the at least one conducting element and/or optionally in the manufacture of the at least one base body, in which at least one green compact is manufactured first, subsequently at least one brown compact is manufactured from said green compact, and subsequently the finished work-piece is manufactured from said brown compact through at least one sintering step. In this context, separate green compacts and/or separate brown compacts can be manufactured for the conducting element and the base body and can be connected subsequently. Alternatively, one or more common green compacts and/or brown compacts can be produced for the base body and the conducting element. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, the one or more binding agents and/or one or more solvents. A brown compact shall be understood to mean a pre-form body which is generated from the green compact through at least one debinding step, for example at least one thermal and/or chemical debinding step, whereby the at least one binding agent and/or the at least one solvent is/are removed, at least partly, from the pre-form body in the debinding step.

The sintering process, for example, of a cermet, but of the base body just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the bushing according to one embodiment, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate.

For the bushing according to one embodiment, the at least one metallic component of the cermet can include, for example, at least one of the following metals and/or an alloy based on at least one of the following metals: platinum, iridium, niobium, molybdenum, tantalum, a tantalum alloy, tungsten, a tungsten alloy, titanium, cobalt, chromium, zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content should be 25% by volume and more, in one embodiment 32% by volume, in one embodiment more than 38% by volume, depending on which materials have been selected. The metal content can, for example, be 25% by volume to 80% by volume, in one embodiment 32% by volume to 60% by volume, and in one embodiment 38% by volume to 50% by volume.

In the scope of one embodiment, the terms, "including a cermet," "comprising a cermet," and "cermet-containing", are used synonymously. Accordingly, the terms refer to the property of an element, being that the element contains cermet. This meaning also includes the variant of an embodiment in that the element, for example the conducting element, consists of a cermet, that is, is fully made of a cermet.

In one embodiment, both the at least one conducting element and the base body can include one or more components which are or can be manufactured in a sintering procedure, or the at least one conducting element and the base body are or can both be manufactured in a sintering procedure. For example, the base body and the conducting element are or can be manufactured in a co-sintering procedure, that is, a procedure of simultaneous sintering of these elements. For example, the conducting element and the base body each can include one or more ceramic components that are manufactured, and in one embodiment compacted, in the scope of at least one sintering procedure.

For example, a base body green compact can be manufactured from an insulating composition of materials. This can proceed, for example, by compressing the composition of materials in a mold. In this context, the insulating composition of materials is a powder mass, in which the powder particles illustrate at least minimal cohesion. In this context, the production of a green compact proceeds, for example, through compressing powder masses or through forming followed by drying.

Said procedural steps can also be utilized to form at least one cermet-containing conducting element green compact. In this context, one embodiment can provide that the powder, which is compressed to form the conducting element green compact, is cermet-containing or consists of a cermet or includes at least one starting material for a cermet. Subsequently, the two green compacts —the base body green compact and the conducting element green compact—can be combined. The manufacture of the conducting element green compact and of the base body green compact can just as well proceed simultaneously, for example, by multi-component injection molding, co-extrusion, etc., such that there is no longer a need to connect them subsequently.

While the green compacts are being sintered, they are in one embodiment subjected to a heat treatment below the melting temperature of the powder particles of the green compact. This usually leads to compaction of the material and thus to ensuing substantial reduction of the porosity and volume of the green compacts. Accordingly, in one embodiment of the method the base body and the conducting element can be sintered jointly. Accordingly, in one embodiment there is no longer a need to connect the two elements subsequently.

Through the sintering, the conducting element becomes connected to the base body in one embodiment in a positive fit-type and/or non-positive fit-type and/or firmly bonded manner. This achieves hermetic integration of the conducting element into the base body in one embodiment. In one embodiment, there is no longer a need for subsequent soldering or welding of the conducting element into the base body. Rather, a hermetically sealing connection between the base body and the conducting element is attained through the joint sintering and utilization of a cermet-containing green compact in one embodiment.

One refinement of the method according to one embodiment is characterized in that the sintering includes only partial sintering of the at least one optional base body green compact, whereby said partial sintering can effect and/or include, for example, the debinding step described above. In one embodiment, the green compact is heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to its/their final size. In the scope of said variant of an embodiment, the green compact is sintered only partly in order to attain a certain stability to render the green compact easier to handle.

The starting material used for producing at least one conducting element green compact and/or at least one base body green compact can, for example, be a dry powder or include a dry powder, whereby the dry powder is compressed in the dry state into a green compact and illustrates sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available, for example. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be shaped into a green compact without the application of high pressure.

In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the work-piece.

One or more of the following substances can be used as binding agent—also called binder: thermoplastic and duroplastic polymers, waxes, thermogelling substances; surface-active substances; methyl cellulose, for example. However, other substances can be used just as well, either alternatively or in addition. In this context, these can be used alone or as binding agent mixtures of multiple components of this type. If individual elements or all elements of the bushing (base body green compact, conducting element green compact, feedthough blank) are produced in the scope of an extrusion procedure, the composition of the binding agent should be such that the line of the elements extruded through the nozzle is sufficiently stable in shape for the shape defined by the nozzle to easily be maintained. Suitable binders, also called binding agents, are known to the person skilled in the art.

In contrast, the conducting element according to the prior art usually is a metal wire. A conducting element provided with a cermet, as is in accordance with one embodiment, can be connected easily to other components since it is a ceramic material. Accordingly, green compacts of both the conducting element and other structural elements, for example in the base body, can be produced and subsequently subjected to a sintering process. Alternatively or in addition, at least one common green compact for multiple structural elements can be manufactured just as well. The resulting electrical bushing is not only particularly biocompatible and durable, but also possesses good hermetic sealing properties. Thus, usually no fissures or connecting sites still to be soldered arise between the conducting element and the base body. Rather, sintering results in the base body and the conducting element becoming connected. In one variant of an embodiment therefore provides the at least one conducting element to consist of a cermet. In this variant of an embodiment, the conducting element includes not only components made of cermet, but is fully made of a cermet.

Generally, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing bearing element can proceed, for example, alike a process for homogeneous powders except that, at identical compression force, the metal is usually compacted more strongly than the ceramic material. Compared to sintered hard metals, the cermet-containing conducting element usually illustrates higher resistance to thermal shock and oxidation. The at least one ceramic component can include, for example, as mentioned above, one or more of the following components: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of Ba (Zr, Ti)$O_3$, Ba (Ce, Ti)$O_3$, KNN, KNN—LiSb$O_3$, and KNN—LiTa$O_3$. The at least one metallic component can include, for example, one or more of the following components: platinum, a platinum alloy, iridium, niobium, molybdenum, titanium, cobalt, zirconium, chromium, tantalum, a tantalum alloy, tungsten, a tungsten alloy. One or more other metallic components can be used alternatively or in addition.

As described above, there are multiple ways of connecting the electrical bushing to the housing. These options can also be combined with each other. Accordingly, one option is to directly connect the electrical bushing to the housing, for example in a non-positive fit-type manner and/or positive fit-type manner and/or firmly bonded manner. For example, as described above with respect to embodiment 30, a firmly bonded connection can be implemented between an inside and/or an outside of the housing and the electrical bushing, for example, through at least one solder connection. In order to promote the solder wetting of the electrical bushing, for example, of a ceramic base body of the electrical bushing, at least one metallization of the base body can be provided, for example a metallization that is applied through at least one physical vapor deposition procedure, for example a sputtering procedure. Said metallization can, for example, be or include a gold metallization. Using the firmly bonded connection, for example at least one internal wall of the housing, for example at least one side wall of the housing, can be connected to the base body. Alternatively or in addition, the firmly bonded connection can also be effected to be situated around individual openings or around a plurality of openings of the plug connector element, for example in that said openings, either alone or in groups, are surrounded by a firmly bonded connection to an inside of the housing.

Alternatively or in addition, a connection between the electrical bushing and the housing can be established, as an option, by providing at least one frame by means of which the electrical bushing is connected to the housing. Said frame can be an integral part of the electrical bushing, for example in that it and the electrical bushing are provided in the form of a single part. However, alternatively or in addition, the frame can just as well be provided fully or in part as a separate component or as an integral component of the housing. The frame can, for example, surround the electrical bushing fully or in part. The frame can act as holding element through which the electrical bushing can be integrated into the housing. The frame can, for example, be arranged in the form of a wreath around the electrical bushing. The frame can be connected to the housing and/or the electrical bushing, for example, in a firmly bonded and/or positive fit-type and/or non-positive fit-type manner. For example, the frame can be used to implement a sealed design of a transition between the electrical bushing and the housing.

The optional frame can, for example, be made of an electrically conductive material. As illustrated above, this can, for example, be at least one metallic material, for example one selected from the group of metallic material specified above, whereby combinations of the specified materials are also feasible. However, alternatively or in addition, the holding element can, for example, also include at least one cermet, as before. Moreover, it is conceivable that the conducting element and the holding element are made from the same material. In this variant, the same materials are used for both the conducting element and the holding element. This relates, for example, to a durable, conductive, and biocompatible cermet. Since both the holding element and the conducting element are still to be connected to metallic components, both must include means to be welded or soldered to them. A cermet meeting the pre-requisites specified above can be used for both the holding element and the conducting element in order to obtain a particularly inexpensive electrical bushing.

The optional frame acting as holding element can, for example, include at least one flange, whereby the flange can, for example, be conductive like a metal. The purpose of the flange can be to seal the electrical bushing with respect to a housing of the implantable device. The holding element in one embodiment holds the electrical bushing in the housing. The holding element can, for example, include at least one flange on at least one external side. Said flange can form a bearing, which, for example, is engaged by the housing of the implantable medical device or parts thereof, for example lids and/or housing shells, in one embodiment engaged in a sealing manner. Accordingly, the holding element having the at least one flange attached can have, for example, a U-, T-, L- or H-shaped cross-section. Integrating at least one flange into the holding element ensures that the electrical bushing is integrated into the implantable device in a safe, impact-resistant and durable manner. In addition, the flange can be designed such that the housing or parts thereof can be connected to it in a positive fit-type manner and/or non-positive fit-type manner, for example through at least one clip-like connection.

According to another aspect, one embodiment proposes an implantable medical device having the features described above. Features and details that were described in the context of the electrical bushing and/or the method shall obviously also apply in relation to the implantable medical device. Moreover, the implantable medical device can further include, for example, at least one supply lead, which is also called "lead" or "leads" in English and can be set up to form an electrical plug connection jointly with the plug connector element of the electrical bushing. The lead can, for example, include at least one plug element, for example at least one male and/or at least one female plug element, which can form an electrical plug-in connection with the plug connection element of the electrical bushing. This can, for example, be at least one male plug element which can be plugged into the at least one plug connector element, for example at least one plug element conforming to one or more of the standard mentioned above.

Another aspect of one embodiment proposes a method for the manufacture of an electrical bushing, as illustrated above. Features and details that are described in the context of the electrical bushing shall also apply accordingly in relation to the method according to one embodiment, and vice versa. With regard to the steps of the method, reference shall be made to the description of the embodiments provided above. The method can be carried out, for example, in that the head part includes components made of different materials, for example the first component, which is provided as the same part as the base body and which includes at least one ceramic material. Moreover, the head part can include further materials, for example the second component, which can include, for example, a non-ceramic material, for example a plastic material. For example, one or more of the plastic materials mentioned above can be used.

The contact element can be connected to the first component in a variety of ways, including mechanical and/or electrical connections. For example, the contact element can be plugged-in or inserted into the first component, either fully or in part. For this purpose, the first component can include, for example, one or more receptacles, for example one or more bore holes and/or mounting openings and/or grooves. Moreover, the contact element can also be connected to one or more other components of the conducting element, for example, electrically. Accordingly, the at least one contact element can, for example, be electrically connected to at least one feedthrough element that is embedded into the base body either fully or in part, for example through at least one non-positive fit-type and/or positive fit-type and/or firmly bonded connection.

Moreover, at least one second component of the head part can be connected to the first component. As illustrated above, said second component can, for example, be provided as a pre-fabricated component, for example as a pre-fabricated component that is formed to be complementary to the first component, in order for the two components to jointly provide, for example, the plug connector element and/or a hollow space thereof. However, as illustrated above, alternatively or in addition, the second component can include at least one closure, for example at least one closure in the form of at least one filling agent and/or at least one grouting compound of at least one mounting opening.

The proposed electrical bushing, the implantable medical device, and the methods provide a large number of advantages as compared to known devices and methods of the specified type. Accordingly, a cost-efficient manufacturing method can be implemented which features high process reliability and low waste production at the same time. Simultaneously, the use of ceramic materials allows high mechanical stability and strong sealing against moisture, for example, body fluid, to be implemented. Accordingly, the proposed bushings have a long service life. Simultaneously, unlike in conventional methods, a plurality of procedural steps can be combined and, optionally, automated in the scope of customary ceramic manufacturing procedures.

Figure 2:
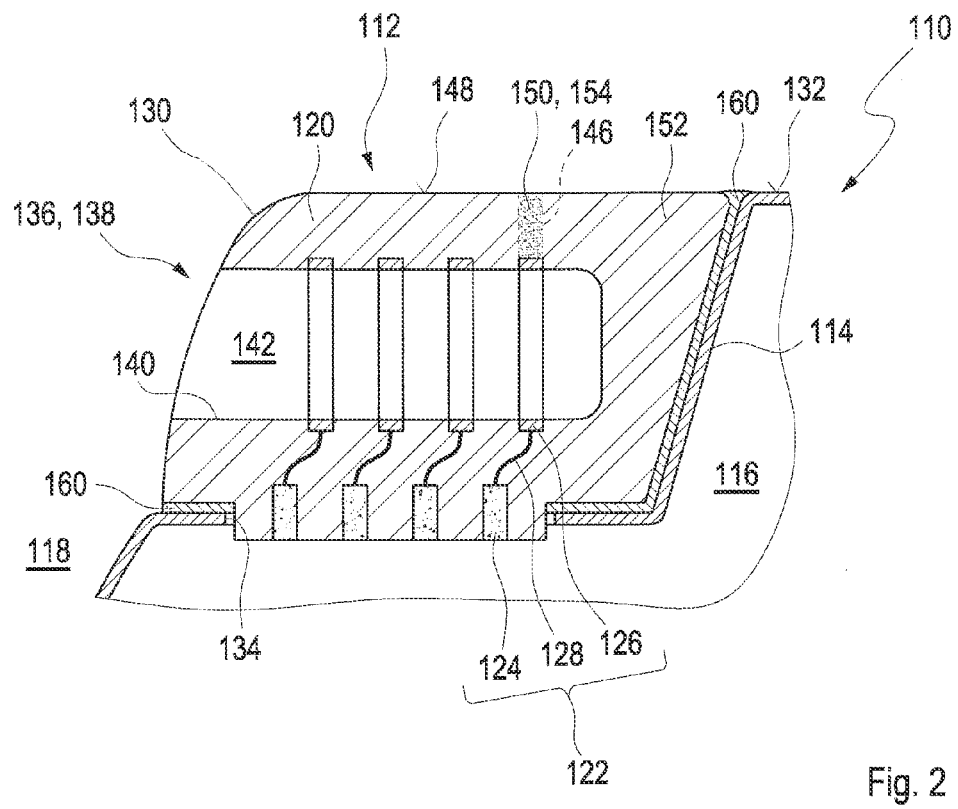

FIGS. 1 and 2 illustrate various views of a first exemplary embodiment of an implantable medical device 110 and an electrical bushing 112 according to one embodiment. In this context, FIG. 1 illustrates a sectional view of the implantable medical device 110 and FIG. 2 illustrates a magnified section of the electrical bushing 112.

The implantable medical device 110 can, for example, be provided as an active implantable medical device, for example according to the prior art illustrated above. With regard to the design of the implantable medical device and its functionality, reference shall be made, for example, to DE 10 2008 021 064 A1 mentioned above. However, other designs are also feasible as a matter of principle.

The implantable medical device 110 includes a housing 114 which surrounds an internal space 116 and separates it from an external space 118. The internal space 116 can accommodate, for example, one or more electrical and/or electromechanical and/or fluidic components, for example one or more components which ensure or support a medical function of the implantable medical device 110. The housing 114 can be provided as a single part or as multiple parts and can be assembled, for example, from one or more housing shells, for example with a separating plane in the plane of the drawing according to FIG. 1.

The implantable medical device 110 further includes the above-mentioned electrical bushing 112. This can be provided, for example, in order to generate a moisture-proof electrical connection between the internal space 116 and the external space, for example to one or more electrodes that are arranged in and can stimulate a heart muscle. For this purpose, the electrical bushing 112 includes a base body 120, in which one or more conducting elements 122 are accommodated. Said conducting elements 122 establish at least one electrically conductive connection between the internals space 116 and the external space 118.

In the exemplary embodiment illustrated, the conducting elements 122 are provided as multiple parts and each include, in exemplary manner, at least one feedthrough element 124, which opens into the internal space 116 or projects into the internal space 116, at least one contact element 126, provided to be ring-shaped in the present case, and at least one connecting element 128 that connects the feedthrough element 124 and the contact element 126. The exemplary embodiment illustrated provides four conducting elements 122. However, it is conceivable that the number of conducting elements 122 is different, for example equal to the numbers specified above.

Moreover, the electrical bushing 112 includes at least one head part 130. Said head part 130 is illustrated in exemplary manner in the exemplary embodiment illustrated here to be provided as the same part as the base body 120 and to be placed-on, for example, from outside onto one external side 132 of the housing 114 such that a part of the head part 130 and/or of the base body 120 projects through a housing opening 134 in the housing 114 into the internal space 116 and/or is accessible from the latter. As shall be illustrated below, other refinements of the head part 130 are feasible just as well. In each case, the feedthrough elements 124 should be contactable from the internal space 116.

The head part 130 includes at least one plug connector element 136, which is provided as a plug socket 138 in the exemplary embodiment illustrated. Said plug socket 138 includes an elongated, for example essentially cylindrical, hollow space 142 that is accessible from the external space 118 through an opening 140, and from which the contact elements 126 are accessible. The contact elements 126 can, for example, surround the hollow space 142 in a ring-shaped manner, as is evident from FIG. 2. The hollow space 142 and its opening 140 can basically take any shape, for example any cross-section, for example, a circular or polygonal cross-section. The head part 130 can include exactly one plug connector element 136 or, just as well and in one embodiment, a plurality of such plug connector elements 136, for example at least two, at least four, at least six, at least ten or even more plug connector elements 136. The plug connector element 136 can conform, for example, fully or in part to one or more of the above-mentioned standards. The plug connector element 136 can be set up to enable electrical connection of at least one plug element situated in the external space 118 to the plug connector element 136. As illustrated above, said plug element, which is not illustrated in FIGS. 1 and 2, can be, for example, a plug element of an electrode or any other type of actuator, which can, for example, be used to stimulate muscle tissue. However, other designs are also feasible as a matter of principle.

The base body 120 has electrically insulating properties. The base body can be made, for example, from an insulating composition of materials, for example, an insulating composition of ceramic materials, for example in accordance with the type described above. The feedthrough elements 124 are made of a cermet, either fully or in part, and are in one embodiment accommodated in the base body 120 in a firmly bonded manner. In one embodiment the same are inserted as green compacts into, and are sintered jointly with, a green compact of the base body 120 or that a joint green compact is produced for the base body 120 and the feedthrough elements 124. The latter can be effected, for example, through a multi-component injection molding procedure or any other forming procedure, in which a multi-component green compact is produced. Subsequently, said joint green compact can be subjected to at least one sintering procedure.

The contact elements 126 can be inserted into the hollow space 142, for example, through the opening 140. However, it is preferred in one embodiment that the base body 120 includes one or more mounting openings through which the contact element(s) 126 can be introduced into the base body 120. This is illustrated in exemplary manner in FIG. 2 through the dashed mounting opening 146, which is shaped, for example, like an elongated slit and leads from an upper side 148 of the head part 130 to the hollow space 142 such that, for example, the ring-shaped contact elements 126 can be inserted into the head part 130 through said one or more mounting openings 146. The mounting opening 146 can subsequently be closed through a closure 150, for example a filling material, for example, a plastic filling material such as, for example, a silicone and/or an epoxy resin and/or a polyurethane. The insertion of the contact element 126 can be effected, for example, after the sintering of the base body 120.

Whereas the feedthrough elements 124 are in one embodiment made from a cermet, the contact elements 126 and the connecting elements 128 are in one embodiment made from at least one metallic material with no ceramic component. For example, the metallic materials specified above can be used for this purpose. FIGS. 1 and 2 illustrate that the connecting elements 128 can be provided, for example, in the form of one or more wires. However, alternatively or in addition, other connections are conceivable just as well, for example in that the contact elements 126 are directly connected to the feedthrough elements 124 and/or are screwed to these or are connected to them through a clamped connection. Various other designs are feasible as well.

The refinement having mounting openings 146 and closures 150 illustrated in FIG. 2 is simultaneously an exemplary embodiment of the head part 130 not necessarily having to be provided as a single part. Accordingly, the base body 120 can include a first component 152 and one or more further components, for example said closure 150, as second component 154. Whereas the first component 152 can, for example, be made from at least one insulating ceramic material or at least one insulating composition of ceramic materials, the second component 154 can, for example, be made from a non-ceramic material, either fully or in part, for example at least one plastic material, as illustrated above.

Figure 3:
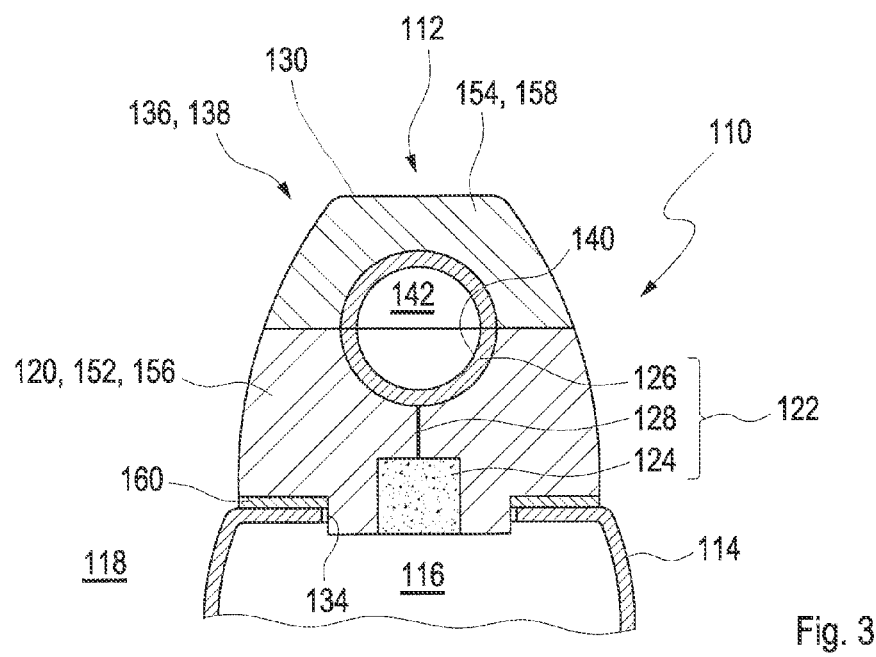
FIG. 3 illustrates a second exemplary embodiment of an implantable medical device having a multi-part head part.

A further exemplary embodiment of a multi-part head part 130 of an implantable medical device 110 is illustrated in FIG. 3. The exemplary embodiment is basically equivalent to the exemplary embodiment illustrated in FIGS. 1 and 2 such that reference to the description provided above shall be made with regard to the functionality of the individual elements. FIG. 3 illustrates a sectional view perpendicular to the sectional plane in FIGS. 1 and 2, that is, a sectional view through the hollow space 142 of the plug socket 138 of the plug connector element 136.

As is evident from the view illustrated according to FIG. 3, the head part 130 is provided as multiple parts in the exemplary embodiment illustrated. Accordingly, the head part 130 includes the electrically insulating base body 120, which has been described above and in which the feedthrough elements 124 are embedded, in one embodiment in a firmly bonded manner. Said base body 120 provides a first component 152 and a lower shell 156 for the plug socket 138. Said first component 152 can, for example, be made in a ceramic procedure. Subsequently, the contact elements 126 can be placed on, for example into corresponding furrows and/or grooves in the lower shell 156. Subsequently, the second component 154 can be placed-on, for example in the form of an upper shell 158 that is provided to be complementary to the lower shell 156 such that the lower shell 156 and the upper shell 158 jointly provide the at least one hollow space 142. The upper shell 158 therefore acts like part of a lid to complete the hollow space 142. The second component 154 can be provided, for example, as a pre-formed component, for example as plastic component and, for example, as injection molded plastic component. Alternatively or in addition, the base body 120 and/or the first component 152 can just as well be placed in a forming tool, and the second component 154 can be formed to it, for example through an injection molding process or a similar forming process.

In the scope of the one embodiment, the terms, upper shell and lower shell, are used generally to mean elements which complement each other to form the plug connector element 136 or a part thereof, for example the plug socket 138 or a part thereof. In this context, nothing shall be specified concerning an orientation of the upper shell 158 and lower shell 156 such that the upper shell 158 and the lower shell 156 can just as well be arranged adjacent to each other or can engage each other.

The plug connector element 136 in the exemplary embodiments illustrated in FIGS. 1 to 3 can include one or more further elements aside from the elements illustrated. Accordingly, for example, one or more clamping springs can be provided, which can ensure a firmly bonded and/or positive fit-type and/or a non-positive fit-type bracketing of a plug element in the plug socket 138. Other elements can be provided as well, for example one or more filter elements, as has been described above. With regard to the design of the plug sockets, reference shall be made, for example, to one or more of the standards illustrated above or the prior art illustrated above, for example, to DE 10 2008 021 064 A1.

Figure 4:
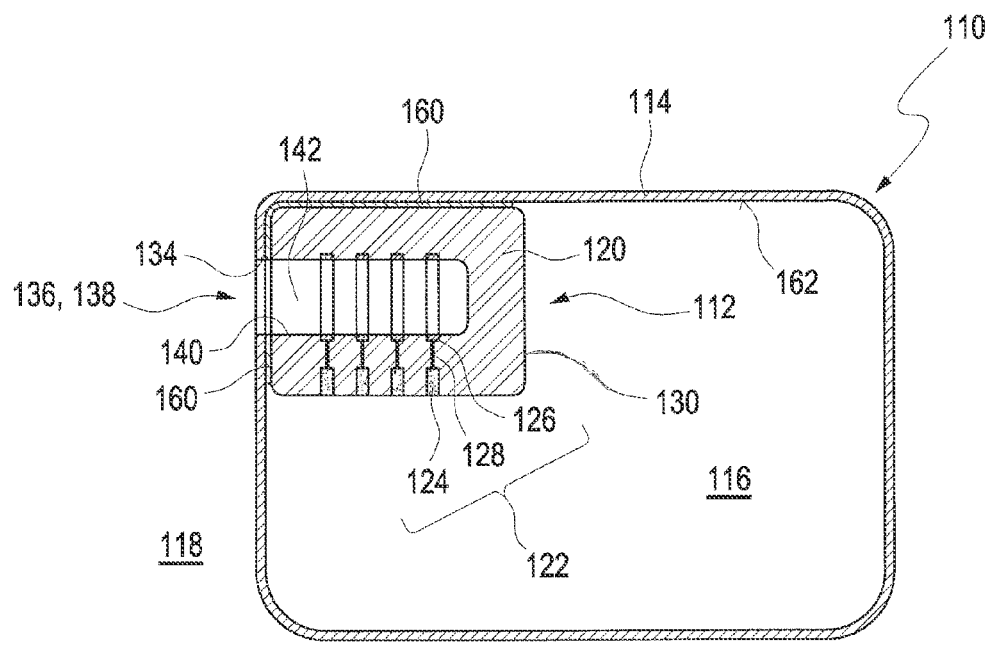
FIGS. 4 and 5 illustrate further exemplary embodiments of an implantable medical device having a head part that is arranged in a housing.
Figure 5:
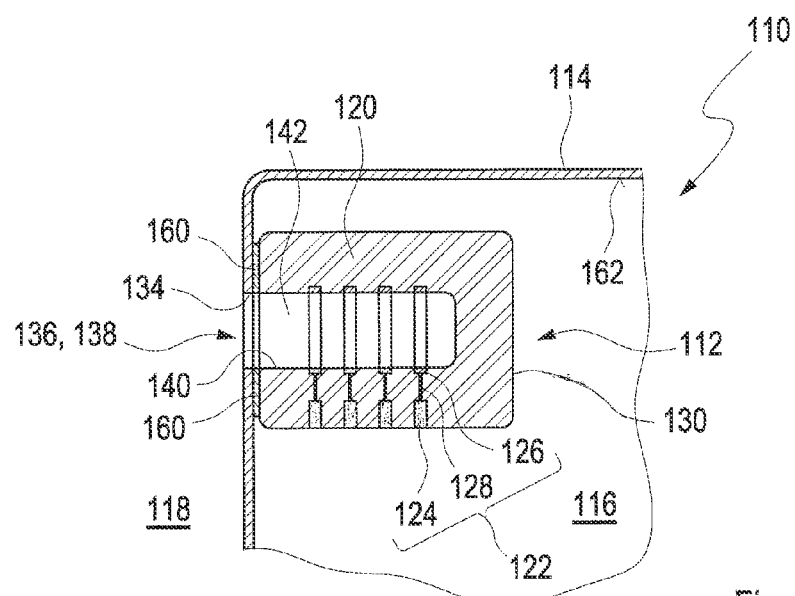

In the exemplary embodiments illustrated according to FIGS. 1 to 3, the head part 130 is placed on the external side 132 of the housing 114. The head part 130 can be connected to the housing 114, for example, in a firmly bonded manner, as illustrated in FIGS. 1 to 3. This can be effected, as illustrated, for example, through at least one solder connection 160. In order to improve the adherence of a solder on the external side of the head part 130, the head part 130, for example the base body 120, can in one embodiment include at least one metallization at least on one or more sides facing the housing 114, which metallization is applied prior to effecting the firmly bonded connection. Due to the high biocompatibility of said material, at least one metallization can be provided, for example, in the form of a gold coating. This is not illustrated in FIGS. 1 to 3. In the exemplary embodiments according to FIGS. 1 to 3, the head part 130 projects into the external space 118. However, this is not necessarily the case in all refinements of embodiments. Accordingly, FIGS. 4 and 5 illustrate exemplary embodiments of implantable medical devices 110, in which again an electrical bushing 112 having a head part 130 is provided. The head part 130 can, for example, again largely correspond to the refinements according to FIGS. 1 to 3 such that reference shall be made to the description provided above with regard to the possible refinements and the meaning of the individual elements. The head part 130 can again be provided as a single part or multiple parts.

A housing opening 134 is again provided in the housing 114. In this context, the view of the exemplary embodiment in FIG. 4 illustrates a sectional view of the entire housing 114, whereas FIG. 5 illustrates just a part of the housing 114 in a sectional view. As is evident from the exemplary embodiments, the head part 130 of the electrical bushing 112 is secured to an inside 162 of the housing 114 such that the opening 140 of the plug socket 138 is accessible through the housing opening 134. This fixation can be effected in a variety of ways. The fixation can again include, for example, a firmly bonded connection, for example a solder connection 160, as illustrated in FIGS. 4 and 5. Whereas the solder connection 160 in the exemplary embodiment according to FIG. 5 is effected just around the opening 140 or around the openings 140 in case multiple openings 140 are provided, either individually or in groups around several of said openings 140, the base body 120 is connected to the inside 114 with much of its surface in the exemplary embodiment according to FIG. 4. In any case, a hermetically sealed connection should be effected such that no moisture can penetrate through the housing opening 134 into the internal space 116. As before, the base body 120 can be provided with at least one metallization prior to connecting it, for example provided with at least one gold metallization, as before.

As a general rule, mixed forms of the exemplary embodiments according to FIGS. 1 to 3 and according to FIGS. 4 to 5 are feasible as well such that, for example, the head part 130 can be partly arranged in the internal space 116 and partly in the external space 118. Moreover, alternatively or in addition to the firmly bonded connection illustrated, other types of connection are conceivable as well, for example non-positive fit-type and/or positive fit-type connections. As before, alternatively or in addition to the connection illustrated, in which the head part 130 is connected directly to the housing 114 through the firmly bonded connection, for example the solder connection 160, the head part 130 can just as well, for example and as illustrated above, be connected to the housing 114 by means of at least one frame. Said frame, which is not illustrated in the Figures, can be designed as a separate component, but it can just as well be connected to the head part 130 and/or the housing 140 before the respective other component is connected. The frame can be, for example, a metallic frame, for example a titanium frame. Other materials are conceivable as well, for example the materials specified above.

Figure 6:
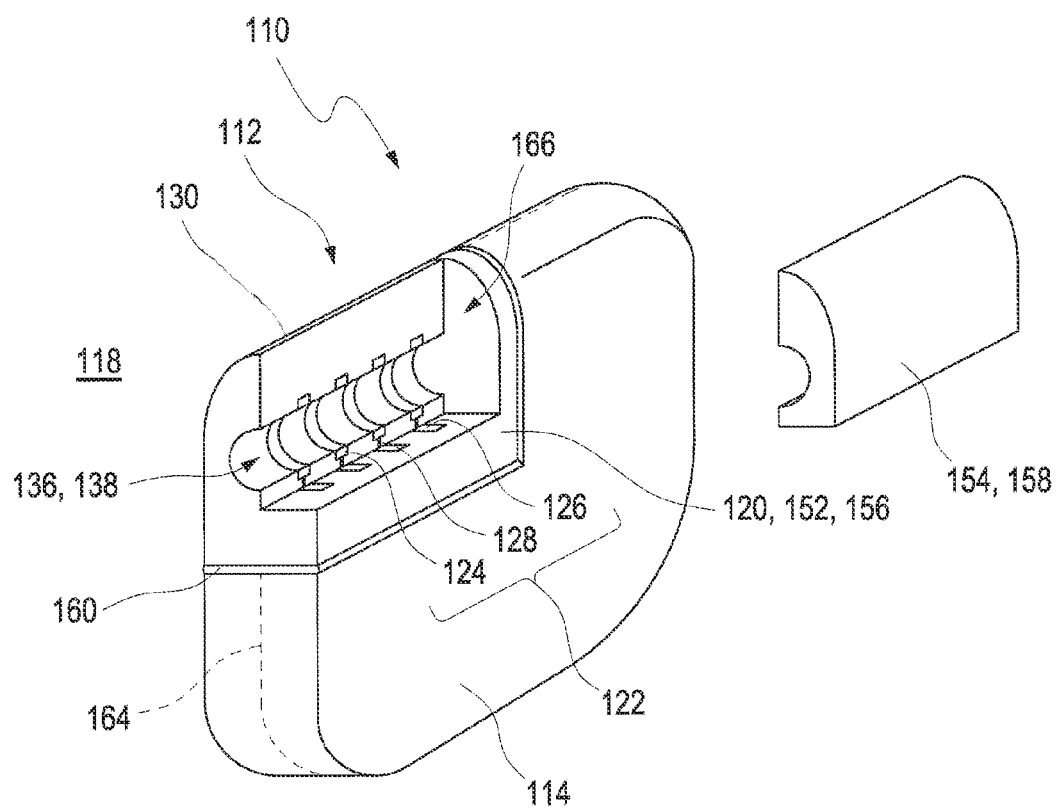
FIGS. 6 and 7 illustrate further exemplary embodiments of an implantable medical device having multi-part head parts.
Figure 7:
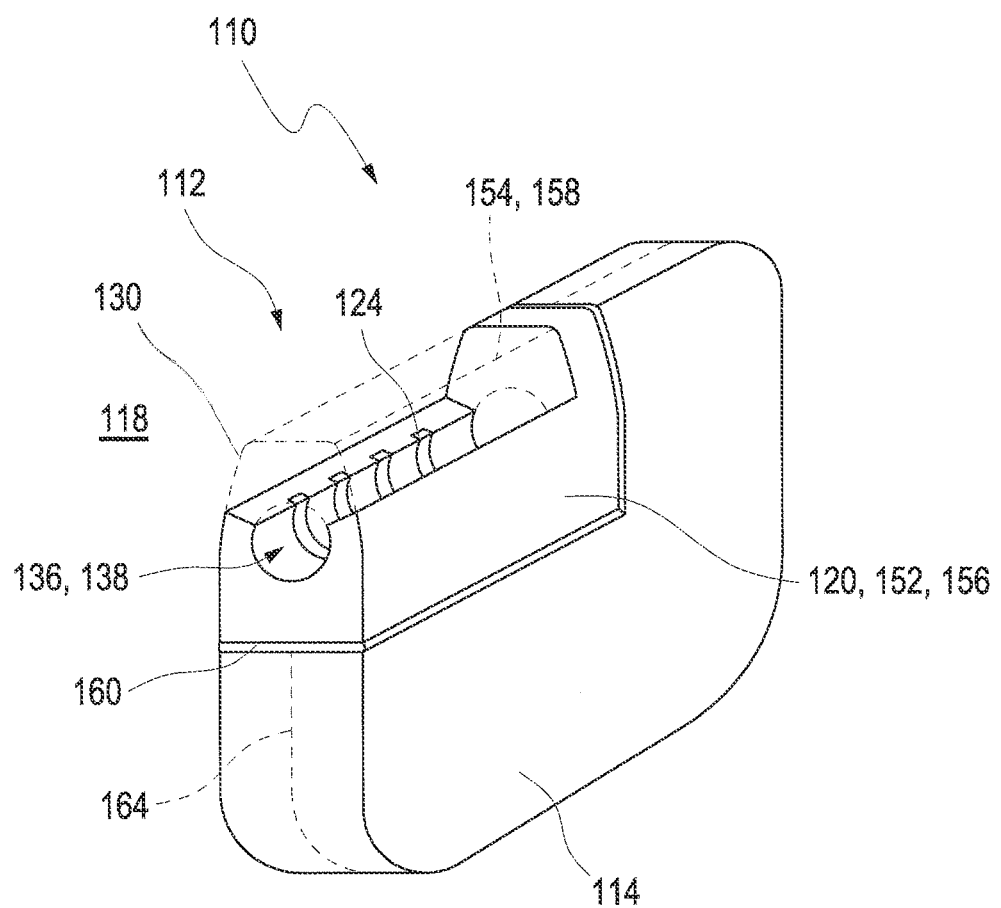

FIGS. 6 and 7 illustrate perspective views of further exemplary embodiments of implantable medical device 110 according to one embodiment having multi-part head parts 130. Said exemplary embodiments can correspond in large parts to the exemplary embodiment according to FIG. 3 such that reference shall be made to the description of FIG. 3 above with regard to the meaning of the individual elements. However, other designs are also feasible as a matter of principle.

The implantable medical devices 110 can again include, for example, a housing 114 which can be composed, for example, of multiple housing parts, for example, housing shells, that are combined for example, at a separating plane 164 or which can just as well be provided as a single part as a general rule. In said separating plane 164, which can include, as a general rule, a separating site and/or separating line and/or any separating area of any shape, the housing parts can be connected to each other, for example, in a firmly bonded manner, in one embodiment be welded to each other. Accordingly, for example at least one welding seam can be present in said separating plane 164. Alternatively or in addition, one or more other connection techniques can be applied just as well, for example non-positive fit-type and/or positive fit-type connections.

Moreover, the implantable medical device 110 in the exemplary embodiments illustrated in FIGS. 6 and 7 again include at least one head part 130, which is provided as multiple parts and which can be connected to the housing 114, for example, through one or more solder connections 160. In this regard, reference shall be made to the description of the remaining exemplary embodiments provided above.

The multi-part head part 130 again includes at least one first component 152, which can, for example, be provided as the same part as the base body 120, and at least one second component 154, which can, for example, be placed on the first component 152 subsequently. The second component 154 can be provided, for example, as a plastic component, either fully or in part.

In the exemplary embodiment according to FIG. 7, the second component 154 is provided, for example, as upper shell 158 in the form of a lid part, and illustrated dashed. The upper shell 158 can, for example, be placed on the first component 152, which can be provided as lower shell 156 and be formed, for example, to be complementary to the upper shell 158, and, for example, be connected to same in a firmly bonded manner, for example through an adhesive connection. Other connection techniques are conceivable as well.

In the exemplary embodiment according to FIG. 6, the second component 154 is illustrated separately, prior to being placed on the first component 152. The second component 154 can, for example, again be provided as lid part or upper shell 158 and can, for example, be inserted into a corresponding recess 166 in the first component 152 such that the first component 152 and the second component 154 can complement each other to provide the plug socket 138. Said exemplary embodiment again illustrates that the terms of upper shell 158 and lower shell 156 are not necessarily to be understood as a spatial orientation, but rather in terms of complementary components. Accordingly, the upper shell 158 can, for example, be placed on the side of the lower shell 156, as illustrated in the exemplary embodiment according to FIG. 6.

Details of the conducting elements 122 are not illustrated in the exemplary embodiment according to FIG. 7. With regard to the manufacture, reference shall be made to the description of FIG. 3 provided above, for example. The feedthrough elements 124 as well as the optional contact elements 126 and the optional connecting elements 128 are illustrated in the exemplary embodiment according to FIG. 6, which illustrates the state with the upper shell 158 taken off. The figure also illustrates, for example, that the contact elements 126 can be inserted and, for example, the connecting elements 128 can be introduced also before placing the second component 154 onto the first component 152. Alternatively, other types of connection can be established between the contact elements 126 and the feedthrough elements 124, whereby reference shall be made to the description provided above in this regard. FIG. 6 only illustrates one each of the contact elements 126 and one of the connecting elements 128 in an exemplary manner. The contact element 126 is again illustrated as a contact element 126 that is provided to be ring-shaped, in exemplary manner. The contact elements 126 can simply be inserted into ring-shaped grooves 168 or any other type of receptacle or simply be placed in or clamped into the first component 152, for example prior to mounting the second component 154, before placing-on the second component 154 and, for example, again connecting it to the first component 152. Refinements without any grooves or receptacles and/or refinements, in which, for example, a positive-fit type linking of the contact elements 126 to the first component 152 and/or the second component 154 is established, for example a welded connection, are feasible as well. Other refinements and/or a different number and/or arrangement of the conducting elements 122 are conceivable as well, for example a number of two, three, five or more conducting elements 122 instead of the four conducting elements 122 and/or contact elements 126 illustrated in FIGS. 6 and 7.

Exemplary Embodiment of Ceramic Compositions:

An exemplary embodiment of a ceramic material for the base body 120 and the at least one electrical conducting element 122 that can be used in the scope of one embodiment is illustrated in the following. However, embodiments shall not be limited to said exemplary embodiment.

In a first step, a cermet mass was produced from platinum (Pt) and aluminum oxide ($Al_2O_3$) containing 10% zirconium dioxide ($ZrO_2$). The following starting materials were used for this purpose:

40 vol. % Pt powder with a mean grain size of 10 μm, and
60 vol. % $Al_2O_3/ZrO_2$ powder with a relative $ZrO_2$ content of 10% and a mean grain size of 1 μm.

The two components were mixed, water and a binding agent were added, and the sample was homogenized through a kneading process.

Analogous to the first step, a ceramic mass was produced in a second step from a powder with an $Al_2O_3$ content of 90% and a $ZrO_2$ content of 10%. The mean grain size was approx. 1 p.m. As before, water and a binding agent were added to the ceramic powder and the sample was homogenized.

In a third step, the ceramic mass made of aluminum oxide with a 10% zirconium dioxide content produced in step 2 was converted to a shape of a base body 120. A cermet body, which was made from the cermet mass produced in step 1 and contained a mixture of platinum powder and aluminum oxide with a zirconium dioxide content of 10%, was introduced as green compact into an opening in the green compact of the base body 120. Subsequently, the ceramic mass was compacted in the mold. Then the cermet and the ceramic component were subjected to debinding at 500° C. and the sintering was finished at 1650° C.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An electrical bushing for a housing of an implantable medical device;
   whereby the electrical bushing comprises at least one electrically insulating base body and at least one electrical conducting element;
   whereby the at least one conducting element comprises a feedthrough element, a contact element and a connecting element and the conducting element establishes, through the base body, at least one electrically conductive connection between an internal space of the housing and an external space;
   whereby the conducting element is hermetically sealed with respect to the base body, at least in part;
   whereby the at least one of the conducting elements comprises at least one cermet;
   characterized in that the electrical bushing comprises at least one head part, whereby the head part comprises at least one plug connector element, whereby the plug connector element enables electrical connection of at least one plug element from the external space to the plug connector element.

2. The electrical bushing according to claim 1, characterized in that the feedthrough element comprises the at least one cermet.

3. The electrical bushing according to claim 1, characterized in that the feedthrough element and the base body are connected in a firmly bonded manner through a firmly bonded sintered connection.

4. The electrical bushing according to claim 1, characterized in that the feedthrough element and the plug connector element are connected in an electrically conductive manner, through at least one connecting element.

5. The electrical bushing according to claim 1, characterized in that the plug connector element comprises at least one plug socket.

6. The electrical bushing according to claim 1, characterized in that the head part is provided as the same part as the base body, at least in part.

7. The electrical bushing according to claim 1, characterized in that the head part is made from an insulating composition of materials, at least in part, whereby the base body is also be made from the insulating composition of materials, at least in part.

8. The electrical bushing according to claim 1, characterized in that the head part comprises at least one first component, whereby the first component and the base body are provided as a single part, whereby the head part further comprises at least one second component, whereby the second component is connected to the first component and, jointly with the first component provides the plug connector element or a part thereof.

9. The electrical bushing according to claim 8, characterized in that the at least one contact element of the conducting element is introduced into the first component through at least one mounting opening of the first component, whereby the second component comprises at least one closure, whereby the closure closes the mounting opening, at least in part.

10. The electrical bushing according to claim 8, characterized in that the second component is made from a plastic material, at least in part.

11. The electrical bushing according to claim 8, characterized in that the first component comprises a lower shell, whereby the second component comprises an upper shell, whereby at least one hollow space of at least one plug socket of the plug connector element, is arranged between the lower shell and the upper shell.

12. An implantable medical device, comprising:
   at least one housing; and
   at least one electrical bushing used in the housing and coupled to the housing,
   whereby the electrical bushing comprises at least one electrically insulating base body and at least one electrical conducting element;

whereby the at least one conducting element establishes, through the base body, at least one electrically conductive connection between an internal space of the housing and an external space;

whereby the conducting element is hermetically sealed with respect to the base body, at least in part;

whereby the at least one conducting element comprises at least one cermet;

characterized in that the electrical bushing comprises at least one head part, whereby the head part comprises at least one plug connector element, whereby the plug connector element enables electrical connection of at least one plug element from the external space to the plug connector element.

13. A method for the manufacture of an electrical bushing whereby the electrical bushing comprises at least one electrically insulating base body and at least one electrical conducting element;

whereby the at least one conducting element comprises a feedthrough element, a contact element and a connecting element and the conducting element establishes, through the base body, at least one electrically conductive connection between an internal space of the housing and an external space;

whereby the conducting element is hermetically sealed with respect to the base body, at least in part;

whereby the at least one of the conducting elements comprises at least one cermet;

whereby the electrical bushing comprises at least one head part, whereby the head part comprises at least one plug connector element, whereby the plug connector element enables electrical connection of at least one plug element from the external space to the plug connector element, characterized in that the method comprises:

a. manufacturing the at least one first component of the head part and of the base body through at least one ceramic manufacturing procedure, whereby the first component and the base body are provided as a single part; and b. connecting at least one contact element of the conducting element to the first component.

14. The method according to claim 13, characterized in that the contact element is to be connected to the at least one feedthrough element that contains the cermet and is embedded in the base body.

15. The method according to claim 13 further comprising:

c. connecting at least one second component of the head part to the first component.

16. The method according to claim 15, characterized in that the second component is provided, at least in part, as a preformed component which is connected to the first component in step c.

17. The method according to claim 15, characterized in that the second component is formed, at least in part, in procedural step c., through a plastic forming procedure.

18. The method according to claim 15, characterized in that the contact element is introduced into at least one opening in the first component in procedural step b., whereby the opening is closed, at least in part, through at least one closure in the subsequent procedural step c., through at least one grouting, whereby the second component comprises the closure.

* * * * *